United States Patent [19]

Subelka

[11] 4,162,163
[45] Jul. 24, 1979

[54] COATING FOR GOLD OR GOLD ALLOY CASTINGS FOR DENTAL BRIDGES AND CROWNS

[75] Inventor: John C. Subelka, Plainsboro, N.J.

[73] Assignee: Johnson & Johnson, New Brunswick, N.J.

[21] Appl. No.: 870,390

[22] Filed: Jan. 18, 1978

[51] Int. Cl.$^2$ ................................................ C09D 5/38
[52] U.S. Cl. .................................. 106/1.13; 106/1.18; 106/35; 252/514
[58] Field of Search .................... 106/1.13, 1.14, 35, 106/1.18; 32/8, 15; 148/24; 252/514

[56] References Cited

U.S. PATENT DOCUMENTS

| | | | |
|---|---|---|---|
| 3,073,270 | 1/1963 | Johnson et al. | 148/24 |
| 3,832,242 | 8/1974 | Cuthbert | 148/24 |
| 4,010,048 | 3/1977 | Tesk et al. | 148/24 |

*Primary Examiner*—Lorenzo B. Hayes

[57] ABSTRACT

A powder-liquid system for preparing dispersions useful for coating gold and gold alloy castings for dental bridges and crowns which comprises (1) a gold powder and (2) a liquid vehicle suitable for dispersing said gold powder which comprises a solution of a borate salt and a tin salt in an organic solvent.

The gold powder preferably has an average particle size of from between 5 to 16 um, the tin salt is preferably stannous chloride, the borate salt is preferably dilithium tetraborate and the organic solvent is a glycol such as propylene glycol. The gold powder is dispersed in said liquid vehicle at a volume/volume ratio of from $0.5/_1$ to $1.5/_1$ prior to use.

The instant invention also relates to a method for treating the surface of a gold or gold alloy casting for a dental bridge or crown to facilitate the bonding thereto of porcelain and to control the shade of such porcelain which comprises coating the surface with the above dispersion, drying to remove the organic solvent, fusing the gold powder to said surface and oxidizing said fused surface to form an oxide layer with a specific morphology thereon.

10 Claims, No Drawings

COATING FOR GOLD OR GOLD ALLOY CASTINGS FOR DENTAL BRIDGES AND CROWNS

FIELD OF INVENTION

A powder-liquid system for preparing dispersions useful for coating gold and gold alloy castings for dental bridges and crowns which comprises (1) a gold powder and (2) a liquid vehicle suitable for dispersing said gold power which comprises a solution of a borate salt and a tin salt in an organic solvent.

The gold powder preferably has an average particle size of from between 5 to 16 μm, the tin salt is preferably stannous chloride, the borate salt is preferably dilithium tetraborate and the organic solvent is a glycol such as propylene glycol. The gold powder is dispersed in said liquid vehicle at a volume/volume ratio of from 0.5/1 to 1.5/1 prior to use.

The instant invention also relates to a method for treating the surface of a gold or gold alloy casting for a dental bridge or crown to facilitate the bonding thereto of procelain and to control the shade of such porcelain which comprises coating the surface with the above dispersion, drying to remove the organic solvent, fusing the gold powder to said surface and oxidizing said fused surface to form an oxide layer with a specific morphology thereon.

BACKGROUND OF THE PRIOR ART

It is known in the art that it is desirable to treat the surface of gold and gold alloy castings for dental crowns and bridges in order to prevent the gasification of the gold or gold alloy during the bonding of porcelain thereto and to improve the uniformity of the color of said gold or gold alloy to make the shade control of the porcelain more facile.

There are commercial products available for this purpose. Jelenko Prima, for example, from J.F. Jelenko & Co., a Division of Penn Walt is a gold powder which is dispersed in propylene glycol prior to use by the dental technician. The viscosity of propylene glycol is fairly low and therefore the resultant dispersions are not easily painted onto the castings, e.g. dripping makes it more difficult to transfer the gold powder to the casting. Sufficient gold transfer cannot be accomplished in a single application. Wilcote available from Wilkinson Gold Co. is a gold powder which is dispersed in glycerine by a dental technician prior to use. Glycerine has a somewhat higher viscosity then propylene glycol but the viscosity of the dispersions is still too low to eliminate the dripping of the dispersion from the brush during painting.

Britecote*, a system available from Ceramco, Inc., Long Island City, New York, consists of a gold cake comprising gold powder, pectin, dilithium tetraborate, stannous chloride, and hydrochloric acid. This cake is broken up and dispersed in propylene glycol. It has been found that during storage this cake changes and becomes difficult to disperse in propylene glycol. It is believed that this change is due to the pectin which being a natural product may vary from batch to batch and with time. In any event it has been found that the gold powder tends to agglomerate in the cake thereby forming dispersions including highly agglomerated particles of gold. Moreover, the dilithium tetraborate must be varied on a batch to batch basis to obtain a suitable viscosity in the presence of the pectin.

SUMMARY OF THE INVENTION

The instant invention relates to a powder-liquid system for preparing dispersions useful for coating gold and gold alloy castings for dental bridges and crowns which comprises (1) a gold powder and (2) a liquid vehicle suitable for dispersing said gold powder which comprises a solution of a borate salt and a tin salt in an organic solvent.

The gold powder utilized in the system and method of this invention will preferably have an average particle size of from 5 to 16 μm. It has been unexpectedy found that gold powder having an average particle size of from about 5 to 16 μm, when dispersed in the liquid vehicle described below, provides dispersions which do not settle upon standing, flow easily during the painting thereof onto the surface of the gold or gold alloy casting and do not sag or drip when the painted casting is being dried or fused.

Gold powders having the preferred average particle size are articles of commerce and can be made by methods known in the art. For example, these materials are available from Metz Metallurgical, Wilkinson Gold Co. and Matthey Bishop, Inc.

The liquid vehicle may comprise a solution of a borate salt and a tin salt in an organic solvent. The solvent must be easily vaporized within about 1 to 3 minutes from a gold or gold alloy surface at a temperature of less than about 600° F., preferably at from about 300° to 400° F. Such organic solvent must have a sufficient viscosity, e.g. at least about 65 cps, as measured at 25° C., using the Brookfield Viscometer #1 Spindle and of course must be capable of dissolving sufficient amounts of such borate salt and said tin salt so that the objects of this invention may be achieved. Finally, such organic solvent must not be so volatile as to make it difficult for the dental technician to maintain a constant viscosity of his gold dispersion while he is working therewith.

Suitable organic solvents include glycols such as glycerin, propylene glycols, ethylene glycols, etc. It has been found that propylene glycol is the most suitable organic solvent for use in the system of this invention.

The borate salt functions as a fluxing agent to enhance wetting of the surface of the casting by the gold powder during fusion and forms glass particles on the surface during the subsequent oxidation thereof. It is believed that these glass particles enhance the subsequent bonding of the porcelain to the oxidized surface. The borate salt may be selected from the group consisting of alkali and alkaline earth metal borates. The most preferred borate salt, from the standpoint of achieving the above functions as well as its solubility in the preferred organic solvents, is dilithium tetraborate. As pointed out above, the viscosity of the vehicle is important to the paintability of the gold dispersions. Dilithium tetraborate is extremely soluble in the preferred propylene glycol solvent and at the higher concentration levels obtainable substantially increases the viscosity of the solvent. In general, from 8% to 12% by weight dilithium tetraborate is added to the preferred propylene glycol solvent to yield a viscosity of from about 120 to 250 cps.

The tin salt is preferably the chloride, nitrate, etc. only because of the relative economy of using such salts as compared to the carboxylates, acetylacetonates, etc. It has been found that stannous chloride has the best balance of solubility in the preferred organic solvents, without being unduly expensive.

The tin salt may be only slightly soluble in the organic solvent of the vehicle. The tin functions to form an easily oxidizable eutectic alloy with the gold of the powder and the casting. Small amounts of tin are suitable since the oxidation of the coated surface of the casting is only carried out until a monomolecular oxide layer is formed. Amounts of tin in said organic solvent (as metal) may range from as low as 0.001% to 0.5% preferably from 0.01% to 0.1%, by weight of the liquid vehicle. The higher amounts of tin generally impart a yellow color to the liquid vehicle and may be undesirable from an aesthetic standpoint. Moreover, the higher amounts are unnecessary for facilitating the oxidation of the coated surface of the dental casting.

The dental technician may make a useful dispersion of such gold powder in the above described vehicle by mixing 1 part (by volume) of such gold powder with 3 parts (by volume) of such liquid vehicle. Suitable dispersions will comprise from 70.0% to 86.0% weight percent of gold powder dispersed in the liquid vehicle and are characterized as being free from settling during use.

It has been found that the viscosity of the dispersion is preferably between 125 and 250 cps (as measured at 25° C. with a Brookfield Viscometer #1 Spindle) for good paintability. Good paintability shall mean for the purposes of this invention that the dispersion will not drip from the brush when the technician is coating the gold or gold alloy surface of the bridge or crown, the dispersion will flow easily over such surface, and the coating will not sag or drip during subsequent handling of the coated surface, e.g. during the fusion step.

The dental technician will paint the dispersion onto the gold or gold alloy dental casting with a paint brush. He may then dry the coated surface of the casting by heating at a temperature of less than 500° F. preferably 300° F. to 400° F. for from 1 to 3 minutes. The preferred propylene glycol solvent vaporizes readily at such temperatures. The dried casting will then be placed in a muffle furnace to fuse the gold powder to the surface of the dental casting. Fusion may be carried out by heating in air at a temperature of from about 1200° F., continuously increasing at a rate of from about 80 to 100° F. per minute, until a temperature of about 1950° F. is obtained. At this point the dental technician will note that the surface of the casting is bright and shiny and due to the molten gold. The dental technician will then maintain this temperature for about 3 minutes until the mono-molecular oxide layer is formed. The surface of the casting at this point will be gray and dull and if examined carefully it will be noted that glass beads are embedded therein. The dental casting at this point will now be ready for adhering a dental procelain thereto. Methods for adhering dental porcelain to the oxidized dental casting are well known in the art and are not a part of this invention. See, for example, commonly assigned U.S. Ser. No. 722,942 filed Sept. 13, 1976 which is hereby incorporated by reference for the purpose of showing methods of adhering the porcelain to the dental casting. It should be noted, however, that the bonding agent taught therein is not required when the dental cast is treated in the manner of this invention.

The following is a preferred embodiment of the instant invention.

A gold powder having an average particle size of from 12 to 14 microns was dispersed in a liquid vehicle comprising 9% dilithium tetraborate and 0.012% stannous chloride, by weight, in propylene glycol. Equal volumes of the powder and the liquid vehicle were used to make up the dispersion. The dispersing step was carried out by hand stirring with a glass rod. This dispersion was painted onto a dental casting comprising gold. It was found that the dispersion did not drip from the brush and flowed easily and uniformly onto the surface of said casting. The coated casting was then dried at a temperature of 400° F. for one minute by placing in the doorway of a muffle furnace. The dried casting was placed in the muffle furnace and rapidly heated to 1200° F. The heating was continued at a rate increase of 100° F. per minute until a temperature of 1945° F. was reached. The surface of the casting was bright and shiny at this point. After an additional 3 minutes at 1945° F. the surfce of the casting had a grey appearance. Subsequent examination of the surface after removing and cooling to room temperature showed that a mono-molecular layer of oxide had been formed embedded in said oxide layer was glass particles of said borate.

What is claimed:

1. A powder-liquid system consisting of two separate components which are mixed for preparing dispersions useful for coating gold and gold alloy castings for dental bridges and crowns the first component consisting of a gold powder having an average particle size of from 5 to 16 $\mu$m and, as the second component, a liquid vehicle suitable for dispersing said gold powder consisting of a solution of an alkali metal or alkaline earth metal borate salt and a stannous tin salt in an organic solvent selected from the group consisting of glycerine, ethylene glycol and propylene glycol.

2. The system of claim 1 wherein said borate salt is dilithium tetraborate and said organic solvent is a glycol.

3. The system of claim 2 wherein said tin salt is stannous chloride.

4. The system of claim 3 wherein said glycol is propylene glycol.

5. A system according to claim 2 wherein said liquid vehicle includes from 5 to 15% by weight of dilithium tetraborate.

6. A system according to claim 3 wherein said liquid vehicle includes from about 0.004 to about 0.020% by weight of stannous chloride.

7. A system according to claim 1 wherein said liquid vehicle has a viscosity of from 150 to 250 cps at 25° C.

8. A dispersion useful for coating gold and gold alloy castings for dental bridges and crowns consisting of gold powder having an average particle size of from 5 to 16 $\mu$m dispersed in a liquid vehicle consisting of a solution of an alkali metal or alkaline earth metal borate salt and a stannous tin salt in an organic solvent selected from the group consisting of glycerine, ethylene glycol and propylene glycol.

9. The dispersion of claim 8 wherein the volume/volume ratio of gold powder to liquid vehicle is from 0.5/1 to 1.5/1 said borate salt is dilithium tetraborate and said organic solvent is a glycol.

10. A dispersion according to claim 8 wherein said gold powder comprises from 70% to 86% by weight of said dispersion.

* * * * *

UNITED STATES PATENT AND TRADEMARK OFFICE
CERTIFICATE OF CORRECTION

PATENT NO. : 4,162,163
DATED : July 24, 1979
INVENTOR(S) : John C. Subelka

It is certified that error appears in the above-identified patent and that said Letters Patent are hereby corrected as shown below:

In Claim 9 (Col. 4, line 62), after 1.5/1 delete "said borate salt is dilithium tetraborate and said organic solvent is a glycol."

Signed and Sealed this

Twenty-seventh Day of November 1979

[SEAL]

Attest:

RUTH C. MASON
*Attesting Officer*

LUTRELLE F. PARKER
*Acting Commissioner of Patents and Trademarks*